US008658587B2

(12) United States Patent
Behrends et al.

(10) Patent No.: US 8,658,587 B2
(45) Date of Patent: Feb. 25, 2014

(54) CONTAINER WITH A COLLAPSIBLE RECEPTACLE AND A DISINFECTANT COMPOSITION

(75) Inventors: Sabine Behrends, Appen (DE); Henning Reinstorff, Hamburg (DE); Andreas Dettmann, Hamburg (DE)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 390 days.

(21) Appl. No.: 13/024,652

(22) Filed: Feb. 10, 2011

(65) Prior Publication Data

US 2011/0233221 A1 Sep. 29, 2011

(30) Foreign Application Priority Data

Mar. 23, 2010 (DE) .......................... 10 2010 012 638

(51) Int. Cl.
*C11D 1/66* (2006.01)
*C11D 3/26* (2006.01)
*C11D 3/24* (2006.01)
*C11D 3/43* (2006.01)

(52) U.S. Cl.
USPC ........... 510/384; 510/383; 510/387; 510/388; 510/391; 510/421; 510/422; 510/499; 510/504; 510/505; 510/506

(58) Field of Classification Search
USPC ......... 510/383, 384, 387, 388, 391, 421, 422, 510/499, 504, 505, 506; 222/212, 215
See application file for complete search history.

(56) References Cited

U.S. PATENT DOCUMENTS

| 3,170,598 | A | * | 2/1965 | McPherson | 222/36 |
|---|---|---|---|---|---|
| 3,277,013 | A | * | 10/1966 | Gianladis | 510/157 |
| 4,047,642 | A | * | 9/1977 | Nilson | 222/94 |
| 4,272,395 | A | * | 6/1981 | Wright | 510/384 |
| 4,278,206 | A | * | 7/1981 | Prussin | 239/327 |
| 4,850,729 | A | * | 7/1989 | Kramer et al. | 401/183 |
| 5,494,533 | A | * | 2/1996 | Woodin et al. | 134/40 |
| 6,945,428 | B2 | * | 9/2005 | Shimizu et al. | 222/105 |
| 7,393,818 | B2 | * | 7/2008 | McDonnell et al. | 510/161 |
| 7,745,384 | B2 | * | 6/2010 | Perry et al. | 510/253 |
| 7,763,575 | B2 | * | 7/2010 | Weiss et al. | 510/138 |
| 7,915,210 | B2 | * | 3/2011 | Bennett et al. | 510/182 |
| 2006/0079429 | A1 | * | 4/2006 | Blagg | 510/379 |
| 2006/0264344 | A1 | * | 11/2006 | Goldberg et al. | 510/130 |
| 2007/0289614 | A1 | * | 12/2007 | McDonnell et al. | 134/42 |
| 2008/0314933 | A1 | * | 12/2008 | Leonoff | 222/215 |
| 2009/0042757 | A1 | * | 2/2009 | Carling | 510/100 |
| 2009/0197786 | A1 | * | 8/2009 | Perry et al. | 510/191 |

* cited by examiner

*Primary Examiner* — Gregory Delcotto
(74) *Attorney, Agent, or Firm* — Young & Thompson

(57) ABSTRACT

A container has: a) a collapsible receptacle, the wall of which is designed flexibly such that the internal volume of the receptacle is adapted to the volume of a liquid contained therein, and which has an outlet with an outlet valve; and b) in the receptacle a disinfectant composition in the form of a solution with a content of aliphatic alcohol of at most 20% by weight. It is possible that the disinfectant composition is not contaminated with spores or other germs also after the container has been opened, even upon repeated discharge from the container.

23 Claims, 2 Drawing Sheets

CONTAINER WITH A COLLAPSIBLE RECEPTACLE AND A DISINFECTANT COMPOSITION

Figure 1:
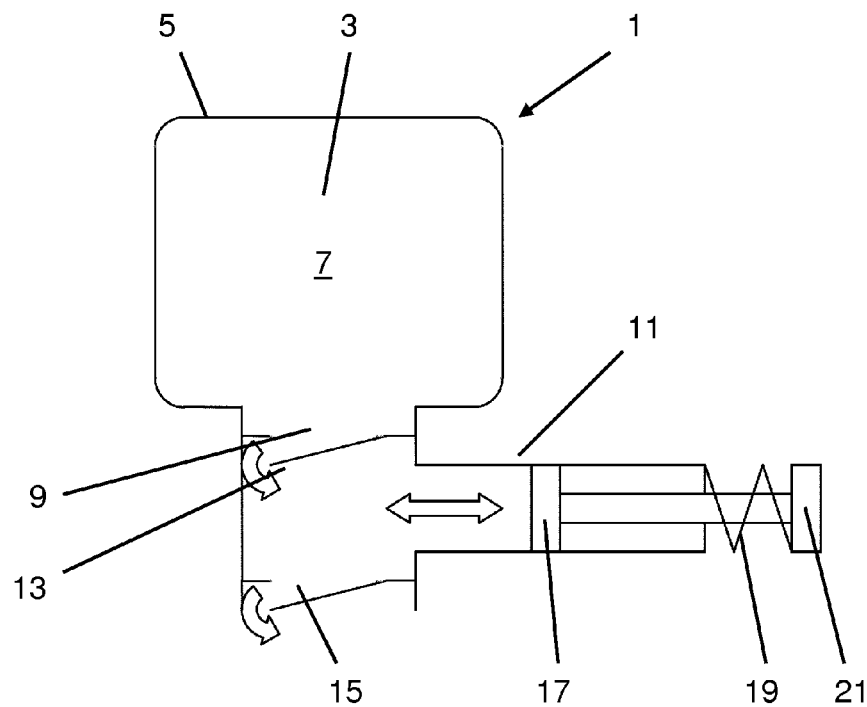

The present invention relates to a container which has a) a collapsible receptacle and b) a disinfectant composition in the receptacle.

Nowadays, containers with antiseptics (such as wound, skin and mucosa antiseptics) and disinfectants (such as hand disinfectants) are used widely; these guarantee and ensure a defined hygiene status until opened. After the container has been opened, however, there is the risk of microbial contamination. However, the user expects the quality of the product to be ensured even after opening. Corresponding requirements can also be found in the guidelines from the Robert Koch Institute (RKI, Berlin, Federal Republic of Germany) for skin disinfectants and surgical hand disinfectants. In the case of antiseptics and disinfectants (which are referred to below as "disinfectant compositions") there is in particular the risk of contamination with spores or other relevant germs after the container has been opened.

The described problem of contamination can be avoided by using containers which are only used once after opening to discharge the disinfectant composition and are then disposed of. However, this leads to a large amount of waste, which is undesirable from an environmental point of view.

Alternatively, disinfectant compositions can be formulated such that after the container has been opened and even upon repeated discharge from the container, contamination with spores or other relevant germs cannot arise. For example, such compositions can be formulated with a high alcohol content. However, this limits the use options of the containers to those applications where a high alcohol content is acceptable. For example, in the case of wound, skin and mucosa antiseptics and hand disinfectants, this is the case only to a limited extent since a high alcohol content leads to the degreasing and irritation of wounds, skin and mucosa.

The object of the present invention was therefore to avoid the aforementioned problems in the prior art and to provide a container comprising a disinfectant composition, where the disinfectant composition is not contaminated with spores or other relevant germs also after the container has been opened and even upon repeated discharge from the container, but without the disinfectant composition inevitably having to be formulated for example with a high alcohol content or high content of antimicrobial active ingredient.

Surprisingly, it has now been found that this object is achieved by a container which has a) a collapsible receptacle, the wall of which is designed flexibly such that the internal volume of the receptacle is adapted to the volume of a liquid contained therein, and which has an outlet with an outlet valve, and b) in the receptacle a disinfectant composition in the form of a solution with a content of aliphatic alcohol of at most 20% by weight.

The invention is based inter alia on the fact that it has been found that the specified disinfectant compositions which, upon contact with air, would possibly not be adequately protected against contamination with spores or other relevant germs can be provided in a container, where the desired high hygiene status is guaranteed also after opening of the container. For example, a high active ingredient content is not obligatory.

Advantages of the containers according to the invention are thus:

improved opening stability in terms of the microbial status and thus increased safety for the user;

the disinfectant compositions are limited to the efficacy spectrum required for the application as regards their formulation (active ingredients in type and amount);

a collapsible container allows the amount of contents to be discerned from outside, even if it is not transparent, i.e. the user can discern whether the required amount of disinfectant can also still be removed from the container;

collapsible receptacles can be manufactured in a simple manner from film material and, as a result of the production methods of films, it is possible to realize with film bags better barrier properties (e.g. in the case of migration-happy, aggressive disinfectants) than e.g. with bottles, thus it is possible e.g. to introduce layers of aluminium into the film, which is not possible in the case of bottles; by contrast, bottles can only be manufactured completely from aluminium, which would be associated with a higher weight and higher costs for the same mechanical properties.

Preferred disinfectant compositions comprise (i) one or more antimicrobial active ingredients selected from quaternary ammonium compounds, biguanides, phenol compounds, halogen compounds and quinoline derivatives. Exemplary active ingredients are selected from bispyridinium alkanes, mecetronium etilsulphate, benzalkonium chloride, alexidine, cetylpyridinium chloride, hexetidine, chlorhexidine salts, polyhexamethylene biguanide salts, o-phenylphenol, 2',4,4'-trichloro-2-hydroxydiphenyl ether (triclosan), PVP-iodine and dequalinium chloride. Octenidine dihydrochloride is preferred as active ingredient in all embodiments of the invention.

The amount of antimicrobial active ingredient, i.e. the sum of all active ingredients (i) is preferably 0.005 to 5% by weight, more preferably 0.01 to 2% by weight, such as in particular 0.03 to 1.0% by weight, for example 0.03 to 0.5% by weight, such as for example 0.05 or about 0.1% by weight.

In addition, the disinfectant composition (ii) can comprise one or more 1- or 2-($C_1$- to $C_{24}$-alkyl) glycerol ethers (glycerol monoalkyl ethers), where the alkyl group of the glycerol monoalkyl ether is preferably a branched or unbranched $C_3$- to $C_{18}$-alkyl group, particularly preferably a 2-ethylhexyl group or a dodecyl group. In particular, 1-(2-ethylhexyl) glycerol ether is preferred.

In one preferred embodiment, the amount of the one or optionally more glycerol monoalkyl ethers, i.e. the total amount of component (ii), is 0.01 to 10% by weight, more preferably 0.03 to 5% by weight, such as about 1% by weight.

Moreover, the disinfectant composition (iii) can comprise one or more polyols. Exemplary polyols are 1,2-propylene glycol, glycerol, erythritol, 1,2,6-hexanetriol, inositol, lactitol, maltitol, mannitol, methylpropanediol, phytanetriol, polyglycerols, sorbitol and xylitol, where glycerol is preferred.

Preferably, the amount of polyol (i.e. the total amount of the optionally two or more polyols) in the composition is 0.01 to 20% by weight, more preferably 0.05 to 10% by weight, such as 0.5 to 5% by weight, for example 2.2 to 2.6% by weight.

Moreover, the disinfectant composition (iv) can comprise one or more nonionic and amphoteric surfactants. Exemplary nonionic surfactants are selected from fatty alcohol ethoxylates, alkyl polyglucosides, amine oxides, ethylene oxide/propylene oxide block copolymers, ether carboxylic acids, preferably fatty alcohol ethoxylates. Exemplary amphoteric surfactants are the betaines, such as e.g. cocamidopropylbetaine.

Exemplary amine oxides have the general formula $R^1R^2R^3N$—O, in which $R^1$ is methyl, ethyl or 2-hydroxyethyl, $R^2$ is methyl, ethyl or 2-hydroxyethyl, $R^1$ and $R^2$ together may be morpholine, $R^3$ is alkyl having 8 to 18 carbon atoms or $R^4CONH(CH_2)_n$, where $R^4$ is alkyl having 8 to 18 carbon atoms and n is in the range from 1 to 10, and 2-hydroxyethyl may be condensed with 1 to 2000 ethylene oxide units, ethylene oxide/propylene oxide units or propylene oxide units, where cocamidopropylamine oxide is particularly preferred as amine oxide.

The amount of nonionic surfactant (i.e. the total amount of the optionally two or more nonionic surfactants) is preferably 0.005 to 1% by weight.

In one particularly preferred embodiment, the disinfectant composition comprises in aqueous solution
i) 0.2 to 0.5% by weight of octenidine dihydrochloride,
ii) 0 to 1% by weight of 1-(2-ethylhexyl) glycerol ether and
iv) 25 to 30% by weight of cocamidopropylamine oxide.

Moreover, the disinfectant composition can comprise (v) one or more auxiliaries and/or additives. Exemplary auxiliaries and/or additives are skincare additives such as allantoin or sodium gluconate, dyes, perfume, buffer, electrolytes and moisturizing factors. The preferred pH of the disinfectant compositions is 4 to 8, more preferably 5 to 6.

Ultimately, the disinfectant composition which is present according to the invention as solution comprises solvent as (vi). Water is particularly preferred as solvent. The amount of solvent is preferably at least 50% by weight, preferably at least 60% by weight, more preferably at least 65% by weight. For example, the composition can comprise more than 75% by weight of solvent, such as more than 80% by weight, more than 85% by weight or more than 90% by weight, in particular at least 97% by weight, of solvent. In particular, water is preferred as solvent.

Disinfectant compositions used according to the invention comprise at most 20% by weight of aliphatic alcohol. Particularly preferred disinfectant compositions are characterized in that they comprise at most 15% by weight of aliphatic alcohol, more preferably at most 10% by weight, in particular at most 5% by weight, of aliphatic alcohol. Alcohols which are encompassed by the term aliphatic alcohols are, for example, ethanol, propan-1-ol, propan-2-ol, and butanols. Particular preference is given to a content of aliphatic alcohol of at most 3% by weight, such as at most 2% by weight, in particular at most 1% by weight. Particularly preferably used disinfectant compositions are free from aliphatic alcohol.

A moreover preferred disinfectant composition comprises
i) 0.02 to 0.2% by weight, such as about 0.05% by weight of octenidine dihydrochloride,
(ii) 0.05 to 5% by weight of 1-(2-ethylhexyl) glycerol ether and
(iii) 1.5 to 4% by weight of glycerol in
(vi) water as solvent in an amount of at least 90% by weight, preferably at least 95% by weight, in particular at least 97% by weight of water,
and optionally
(i) 0.15 to 0.5% by weight of quaternary ammonium compound, preferably cocamidopropylbetaine, benzalkonium chloride or mecetronium etilsulphate,
(iv) 0.015 to 0.05% by weight of nonionic surfactant, preferably laureth-35, and/or
(v) 0.2 to 0.6% by weight of sodium gluconate.

Also preferred as disinfectant composition is one which comprises
(i) 0.001 to 1% by weight of bispyridinium alkane, such as octenidine dihydrochloride, preferably in an amount of from 0.01 to 0.5% by weight, more preferably 0.05 to 0.2% by weight, in particular 0.08 to 0.12% by weight, such as about 0.1% by weight, and
(iii) polyol, such as glycerol, preferably in an amount of from 1.5 to 3.5% by weight, more preferably 2.0 to 3.0% by weight, in particular 2.2 to 2.6% by weight, such as 2.3 to 2.5% by weight, such as about 2.4% by weight, in
(vi) water as solvent,
where the composition
has an osmolality of from 230 to 350 mOsmol/kg and
is free from surfactant.

Particularly preferred disinfectant compositions are free from alcohol, where the term alcohol in this connection includes aliphatic and also aromatic alcohols.

Moreover, preferred disinfectant compositions are free from inorganic salts.

In one preferred embodiment, the osmolality of the composition is 260 to 320 mOsmol/kg, in particular 270 to 310 mOsmol/kg.

Applications of the disinfectant compositions used according to the invention are in particular in disinfectant hand washing, in particular as skin antiseptic. The compositions are suitable for surgical hand disinfection, hygiene hand washing, hand decontamination, skin decontamination, mucosa decontamination, intimate washing lotion, as antimicrobial washing lotion, for (whole) body washing and care in the case of MRSA (Methicillin-resistant *Staphylococcus aureus*), and also moreover for disinfectant hand washing, for hygiene catheter care in patients, as hand washing preparation, such as, for example, as antimicrobial soap, hand washing gel or hand washing lotion. They can be washed advantageously in all areas with increased hygiene requirements in the medical and nonmedical sector, e.g. hospitals, doctors' surgeries, homes for the elderly and care homes, and also food and kitchen sector.

Compositions used according to the invention can also be used as wound and mucosa antiseptic, both for people and also for animals. Examples of animals for which the composition can be used are all vertebrates. The use can also take place in ultrasound-associated wound treatment (UAW).

Preferred receptacle materials are polyethylene, polypropylene, polyester, polyvinyl chloride, poly(meth)acrylate, silicones, optionally with coatings made of or comprising aluminium and/or silver, and/or with barrier layers made of polysiloxanes. In particular, films with a corresponding layered structure can be used.

As explained above, the container has a collapsible receptacle, the wall of which is designed flexibly such that the internal volume of the receptacle adapts to the volume of a liquid contained therein, and which has an outlet with an outlet valve. The fact that a collapsible receptacle is used ensures that no possibly contaminated air passes into the container with the disinfectant composition. Surprisingly, this measure has proven to be sufficient to achieve a significant improvement in hygiene properties, meaning that the hygiene status of the composition is retained also after the first opening of the container and after removing some of the composition.

It is preferred that a manually operated pump, preferably a piston pump, is provided at the outlet of the receptacle. In this case, on the one hand, the amount of discharged composition can be metered easily, and on the other hand it is possible using the pump in a simple manner to remove the composition from the collapsible receptacle and to apply the required force so that its wall is deformed corresponding to the changing internal volume. As an alternative to a manually operated piston pump, it is also possible to provide a motor-driven pump, which, like the piston pump, also works as outlet valve.

In one alternative embodiment, a non-return valve is provided at the outlet; this is opened at an internal pressure in the receptacle which is above a pregiven threshold and is otherwise closed. In such an arrangement, the receptacle is deformed by pressure from outside corresponding to the required change in internal volume, the non-return valve ensuring that the wall cannot "spring back" into a position where the internal volume exceeds the volume of the remaining composition, meaning that ambient air is drawn into the receptacle.

In a further alternative embodiment, the receptacle is surrounded by an elastically deformable outer container so that a closed intermediate volume is formed between the outer container and the receptacle, and in the wall of the outer container a non-return valve is arranged which is opened in the event of a subatmospheric pressure in the intermediate volume and is otherwise closed. In addition, a non-return valve is provided at the outlet which is opened in the event of an internal pressure in the receptacle which is above a pregiven threshold, and is otherwise closed.

In an arrangement of this type, it is possible, in each case starting from an unchanged shape of the outer container, to exert pressure on the receptacle such that the non-return valve attached to its outlet opens and the composition flows out. If no more pressure is exerted on the outer container, no more composition flows out, but the non-return valve at the outlet closes while the non-return valve opens to the intermediate volume so that the outer container can return to its starting position. With such a structure, the container can be operated easily, and ambient air is nevertheless prevented from passing into the inside.

Figure 2:
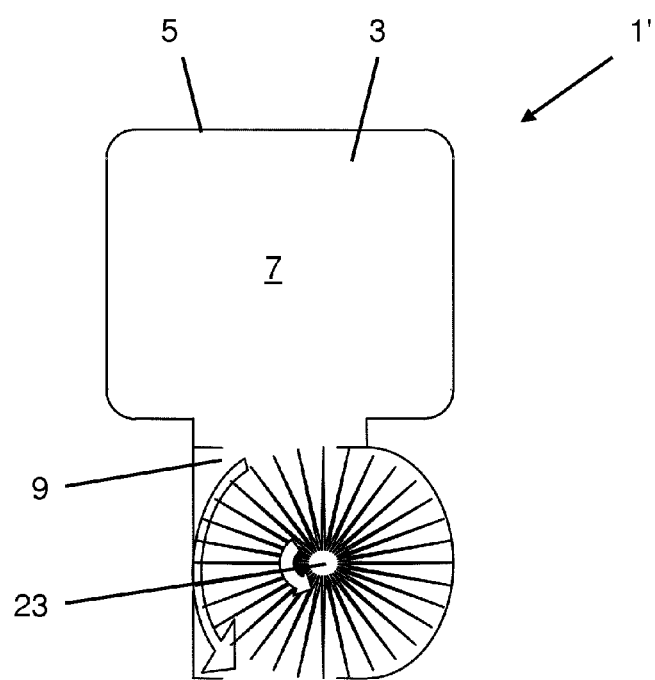
Figure 3:
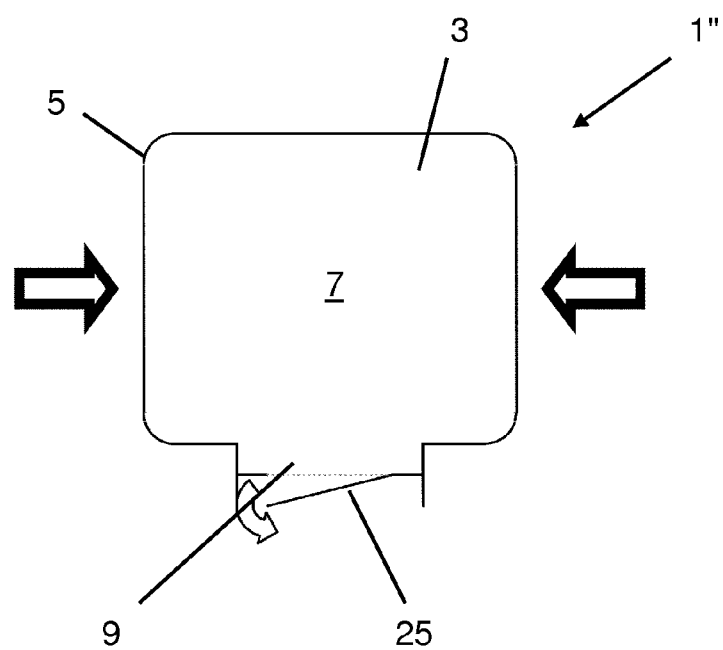
Figure 4:
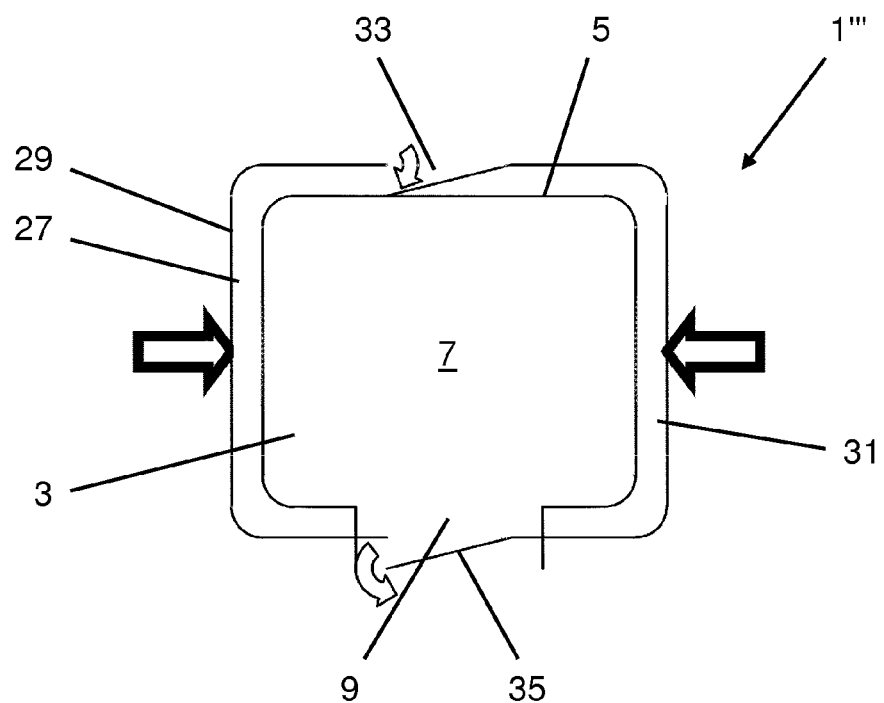

The present invention is described below by reference to a drawing, which shows a number of preferred embodiments, where FIG. 1 shows a cross sectional view of a first preferred embodiment of a container according to the invention, FIG. 2 shows a cross sectional view of a second preferred embodiment of a container according to the invention, FIG. 3 shows a cross sectional view of a first preferred embodiment of a container according to the invention and FIG. 4 shows a cross sectional view of a first preferred embodiment of a container according to the invention.

FIG. 1 shows a first embodiment of a container 1 according to the invention with disinfectant composition, said container having a collapsible receptacle 3 which is completely filled with the disinfectant composition described above and the wall 5 of which is flexible such that the internal volume 7 of the receptacle 3 adapts to the volume of a liquid contained therein, in this case the disinfectant composition. This means that as the composition flows out of the receptacle 3, the latter collapses, i.e. collapses, and its internal volume 7 decreases more and more.

Here, the material of the wall 5 of the receptacle 3 can be selected from polyethylene, polypropylene, polyester, polyvinyl chloride, poly(meth)acrylate, silicones, optionally with coatings made of or comprising aluminium and/or silver, and/or with barrier layers made of polysiloxanes. Flexible materials made of nonpolar polymers such as polyethylene, polypropylene, copolymers or mixtures (blends) thereof are highly suitable since here no interactions with e.g. cationic active ingredients arise. In particular, a corresponding film material can be used as material for the wall of the receptacle.

Furthermore, the receptacle 3 has an outlet 9 to which is attached, in this embodiment preferred in this respect, a manually operated piston pump 11. The piston pump 11 has a first non-return valve 13 pointing to the internal volume, a second non-return valve 15 pointing to an outflow, which acts as outlet valve, and also a pump piston 17 which is pretensioned by a spring 19 and which is connected to an operating element 21.

If the pump piston 17 is pressed in against the pretension of the spring 19 into the pump housing, the composition located between the non-return valves 13, 15 is forced out through the outflow since the second non-return valve 15 opens whereas the first non-return valve remains closed. If the pump piston 17 is no longer supplied with a force via the operating element 21, it moves back on account of the spring pretension, such that the second non-return valve 15 closes, but the first non-return valve 13 opens so that composition can then flow from the internal volume 7 of the receptacle 3 into the intermediate space between the non-return valves 13, 15.

In the case of such a design of the container 1 with a piston pump 11, on the one hand the amount of discharged composition can be easily metered. On the other hand, however, it is ensured that it is possible for a user to easily apply the force which is required to deform the wall 5 of the receptacle 3 so that its internal volume is always adapted to the volume of the composition contained therein.

The second embodiment of a container 1' according to the invention shown in FIG. 2 and filled with disinfectant composition differs from that described above in that, instead of a manually operated piston pump, here a motor-driven pump 23 is used in order to pump composition from the internal volume 7 of the collapsible receptacle 3 through the outlet 9. The pump 23 works here also as outlet valve. In this case, the user himself does not have to apply any force in order to deform the wall 5 of the receptacle 3 corresponding to the decrease in volume of the composition contained therein.

In the embodiment shown in FIG. 3, the collapsible receptacle 3 of the container 1" is provided with an outlet non-return valve 25 which opens at an internal pressure in the receptacle 3 which is above a pregiven threshold and is otherwise closed. Such a container 1" can, in order to discharge the composition, be pressed easily, for example in the direction of the arrow, in which case, on account of the internal pressure which arises, the outlet non-return valve 25 opens and the composition flows out. If no further pressure is exerted on the wall 5, the outlet non-return valve 25 closes, and as a result the ambient air is prevented from being able to flow into the internal volume 7 of the receptacle 3. This reliably prevents the hygiene state of the composition deteriorating.

The embodiment of a container 1''', which is shown in FIG. 4, has, besides the collapsible receptacle 3, also an outer container 27, the wall of which 29 is elastically deformable. The outer container 27 surrounds the receptacle 3 where, between the wall 29 of the outer container 27 and the wall 5 of the receptacle 3, an intermediate volume 31 is enclosed. Finally, a non-return valve 33 is provided in the wall 29 of the outer container 27; this opens in the event of a subatmospheric pressure in the intermediate volume 31 and is otherwise closed. Furthermore, a non-return valve 35 is provided at the outlet 9 of the receptacle 3.

According to the fourth embodiment, the container 1''' can be operated by exerting pressure on the wall 29 of the outer container 27, for example in the direction of the arrow. Since in this case the non-return valve 33 remains closed, the receptacle 3 is likewise squeezed, and the composition flows out through the opening non-return valve 35. If no further pressure is exerted on the wall 29 of the outer container 27, the non-return valve 35 closes, and on account of the elasticity of the wall 29, the latter endeavours to return to its starting state, thus giving rise to a subatmospheric pressure in the intermediate volume 31. This in turn leads to the non-return valve 33 opening, so that the wall 29 of the outer container 27 can return to its starting state without the wall 5 of the receptacle 3 having to follow it. The intermediate volume 31 is therefore "topped up" via the non-return valve 33.

A structure of this type has the advantage that a user can discharge composition from the receptacle 3 always starting from the same shape of the outer container 27 without the risk of ambient air coming into contact with the composition located in the internal volume 7 of the receptacle 3 and impairing its hygiene state.

The embodiments of containers described above result in the disinfectant compositions specified at the start, which, upon contact with air, would possibly not be adequately protected against contamination with spores or other relevant germs, being able to be provided in such a container, where the desired high hygiene status continues to be ensured also after the container has been opened.

The invention claimed is:
1. A container comprising:
   a collapsible receptacle, a wall of which is designed flexibly such that an internal volume of the receptacle is adapted to the volume of a liquid contained therein,
   the receptacle comprising an outlet with an outlet valve, with a manually operated pump provided at the outlet, wherein said manually operated pump comprises:
      a first non-return valve pointing to the internal volume,
      a second non-return valve pointing to an outflow, and
      a pump piston that is pretensioned by a spring and connected to an operating element, and
   in the receptacle, a disinfectant composition in the form of a solution with a content of aliphatic alcohol of at most 20% by weight.
2. Container according to claim 1, characterized in that the disinfectant composition comprises one or more antimicrobial active ingredients selected from quaternary ammonium compounds, biguanides, phenol compounds, halogen compounds and quinoline derivatives.
3. Container according to claim 2, characterized in that the antimicrobial active ingredient is selected from bispyridinium alkanes, mecetronium etilsulphate, benzalkonium chloride, alexidine, cetylpyridinium chloride, hexetidine, chlorhexidine salts, polyhexamethylenebiguanide salts, o-phenylphenol, 2',4,4'-trichloro-2-hydroxydiphenyl ether (triclosan), PVP-iodine and dequalinium chloride, in particular octenidine dihydrochloride.
4. Container according to claim 2, characterized in that the composition comprises 0.01 to 2% by weight of antimicrobial active ingredient.
5. Container according to claim 1, characterized in that the disinfectant composition also comprises one or more 1- or 2-($C_1$- to $C_{24}$-alkyl) glycerol ethers (glycol monoalkyl ethers), where the alkyl group of the glycerol monoalkyl ether is preferably a branched or unbranched $C_3$- to $C_{18}$-alkyl group, particularly preferably a 2-ethylhexyl group or a dodecyl group, in particular 1-(2-ethylhexyl) glycerol ether.
6. Container according to claim 5, characterized in that the disinfectant composition comprises 0.03 to 5% by weight of glycerol monoalkyl ether.
7. Container according to claim 1, characterized in that the disinfectant composition also comprises one or more polyols.
8. Container according to claim 7, characterized in that the polyol is selected from 1,2-propylene glycol, glycerol, erythritol, 1,2,6-hexanetriol, inositol, lactitol, maltitol, mannitol, methylpropanediol, phytantriol, polyglycerols, sorbitol and xylitol, with glycerol being preferred.
9. Container according to claim 7, characterized in that the disinfectant composition comprises 0.05 to 10% by weight of polyol.
10. Container according to claim 1, characterized in that the disinfectant composition also comprises one or more nonionic and amphoteric surfactants.
11. Container according to claim 10, characterized in that the nonionic surfactant is selected from fatty alcohol ethoxylates, alkyl polyglucosides, amine oxides, ethylene oxide/propylene oxide block copolymers, and ether carboxylic acids, preferably fatty alcohol ethoxylates.
12. Container according to claim 11, characterized in that the amine oxide has the general formula

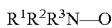

in which $R^1$ is methyl, ethyl or 2-hydroxyethyl, $R^2$ is methyl, ethyl or 2-hydroxyethyl, $R^1$ and $R^2$ together may be morpholine, $R^3$ is alkyl having 8 to 18 carbon atoms or $R^4CONH(CH_2)_n$, where $R^4$ is alkyl having 8 to 18 carbon atoms and n is in the range from 1 to 10, and 2-hydroxyethyl can be condensed with 1 to 2000 ethylene oxide units, ethylene oxide/propylene oxide units or propylene oxide units, where cocamidopropylamine oxide is particularly preferred as amine oxide.
13. Container according to claim 10, characterized in that the disinfectant composition comprises 0.005 to 1% by weight of nonionic surfactant.
14. Container according to claim 11, characterized in that the disinfectant composition comprises in aqueous solution
   i) 0.2 to 0.5% by weight of octenidine dihydrochloride,
   ii) 0 to 1% by weight of 1-(2-ethylhexyl) glycerol ether and
   iv) 25 to 30% by weight of cocamidopropylamine oxide.
15. Container according to claim 1, characterized in that the disinfectant composition also comprises one or more auxiliaries and/or additives.
16. Container according to claim 1, characterized in that the disinfectant composition also comprises solvent, where water is particularly preferred as solvent.
17. Container according to claim 1, characterized in that the disinfectant composition comprises at most 15% by weight of aliphatic alcohol, preferably at most 10% by weight, in particular at most 5% by weight, of aliphatic alcohol.
18. Container according to claim 2, characterized in that the disinfectant composition comprises
   (i) 0.02 to 0.2% by weight of octenidine dihydrochloride,
   (ii) 0.05 to 5% by weight of 1-(2-ethylhexyl) glycerol ether and
   (iii) 1.5 to 4% by weight of glycerol in
   (vi) water as solvent in an amount of at least 90% by weight, preferably at least 95% by weight, in particular at least 97% by weight of water,
   and optionally
   (i) 0.15 to 0.5% by weight of quaternary ammonium compound, preferably cocamidopropylbetaine, benzalkonium chloride or mecetronium etilsulphate,
   (iii) 0.015 to 0.05% by weight of nonionic surfactant, preferably laureth-35, and/or
   (v) 0.2 to 0.6% by weight of sodium gluconate.
19. Container according to claim 2, characterized in that the disinfectant composition comprises
   (i) 0.001 to 1% by weight of bispyridinium alkane, preferably octenidine dihydrochloride, preferably in an amount of from 0.03 to 0.5% by weight, more preferably 0.05 to 0.2% by weight, in particular 0.08 to 0.12% by weight, such as about 0.1% by weight, of component i), and (iii) polyol, preferably glycerol, preferably in an amount of from 1.5 to 3.5% by weight, more preferably 2.0 to 3.0% by weight, in particular 2.2 to 2.6% by weight, such as 2.3 to 2.5% by weight, such as about 2.4% by weight, of component ii), in (vi) water as solvent, where the composition has an osmolality of from 230 to 350 mOsmol/kg and is free from surfactant.

20. Container according to claim 1, characterized in that the disinfectant composition is free from alcohol.

21. Container according to claim 1, characterized in that the disinfectant composition is free from inorganic salts.

22. Container according to claim 1, characterized in that the osmolality of the composition is 260 to 320 mOsmol/kg, in particular 270 to 310 mOsmol/kg.

23. Container according to claim 1, characterized in that the material of the receptacle is selected or is combined from polyethylene, polypropylene, polyester, polyvinyl chloride, poly(meth)acrylate, silicones, optionally with coatings made of or comprising aluminium and/or silver, and/or with barrier layers made of polysiloxanes.

* * * * *